United States Patent

Adam et al.

[11] Patent Number: 6,020,525
[45] Date of Patent: Feb. 1, 2000

[54] (2S,2'R,3'R)-2-(2,3-DICARBOXYL-CYCLOPROPYL)-GLYCINE (DCG-1/4) AND $^3$H-DCG-1/4 AND TO PROCESS FOR THE PREPARATION THEREOF

[75] Inventors: Geo Adam, Schopfheim, Germany; Philippe Nicolas Huguenin-Virchaux, Liestal, Switzerland; Jurgen Wichmann, Steinen, Germany

[73] Assignee: Hoffmann-La Roche Inc., Nutley, N.J.

[21] Appl. No.: 09/256,047

[22] Filed: Feb. 23, 1999

[30] Foreign Application Priority Data

Mar. 19, 1998 [EP] European Pat. Off. .............. 98104992

[51] Int. Cl.$^7$ ..................................................... C07C 61/04
[52] U.S. Cl. ................................................................. 562/506
[58] Field of Search ............................................... 562/506

[56] References Cited

FOREIGN PATENT DOCUMENTS

WO 91/15858  10/1991  WIPO .
WO 93/08158  4/1993  WIPO .

OTHER PUBLICATIONS

Database CAPLUS on STN, Acc. No. 1995:15890, Shimamoto et al., 'Synthesis of conformationally constrained glutamate analogs.' Tennen Yuki Kagobutsu Toronkai Koen Yoshishu (1993), 35th, p559–66 (abstract), 1995.
Database CAPLUS of STN, Acc. No. 1994:606018, Nakanishi et al., 'Preparation of 2-(2,3-dicarboxycyclopropyl)glycine stereoisomers and G protein-coupled glutamatergic receptor agonists containing them.' JP 06024970 (abstract), 1994.
F. Sladeczek et al., Nature, 317:717–719 (1985).
F. Nicoletti et al., Journal of Neurochemistry, 46(1):40–46 (1986).
Y. Ohfune et al., Bioorganic & Medicinal Chemistry Letters, 3(1):15–18 (1993).
K. Shimamoto et al., J. Med. Chem., 39:407–423 (1996).
F. Feist, Chem. Ber., 26:747–764 (1893).
A. Blomquist et al., J. Am. Chem. Soc., 81:2012–2017 (1959).
W. Doering et al., Tetrahedron, 26:2825–2835 (1970).
J. Neff et al., J. Org. Chem., 39(26):3814–3819 (1974).
T. Gilchrist et al., Journal of the Chemical Society (C), p. 776–778 (1968).
M. Ettlinger et al., Journal of the American Chemical Society, 74(22):5805–5806 (1952).

*Primary Examiner*—Gary Geist
*Assistant Examiner*—Brian J. Davis
*Attorney, Agent, or Firm*—George W. Johnston; Patricia S. Rocha-Tramaloni; Eileen M. Ebel

[57] ABSTRACT

This invention relates to (2S,2'R,3'R)-2-(2,3-dicarboxyl-cyclopropyl)-glycine of formula

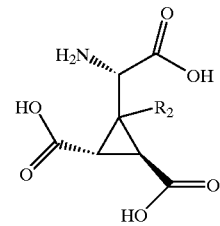

wherein R$_2$ is hydrogen or tritium and to a process for the preparation thereof. The described compounds can be used as a pharmacological tool to study the function of group II mGluR (metabotropic glutamate receptor).

13 Claims, No Drawings

(2S,2'R,3'R)-2-(2,3-DICARBOXYL-CYCLOPROPYL)-GLYCINE (DCG-1/4) AND ³H-DCG-1/4 AND TO PROCESS FOR THE PREPARATION THEREOF

FIELD OF THE INVENTION

The present invention relates to a compound of formula I and a process for its preparation of (2S,2'R,3'R)-2-(2,3-dicarboxylcyclopropyl)-glycine (DCG-¼) and ³H-DCG-¼

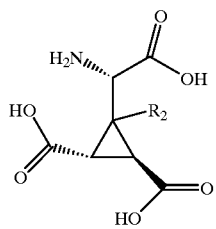

I wherein $R_2$ is hydrogen or tritium.

DCG-¼ can be used as a pharmacological tool to study the function of group II mGluR (metabotropic glutamate receptor). ³H-DCG-¼ is useful in establishment of a radioligand binding assay and to study the distribution of group II mGluR in the brain. The mGluR is an exitatory amino acid (EAA) receptor which mediates synaptic excitation in the mammalian central nervous system.

BACKGROUND OF THE INVENTION

After the independent discovery of the first mGluR by Sladeczeck et al. (Nature, 317, p. 245 (1985) and by Nicoletti et al. (Jour. Neuro. Chem., 46, p. 40, (1986), the multiplicity of this class has been disclosed by expression cloning studies. Currently, eight mGluRs (and several splice variants) have been isolated and subdivided in three groups according to sequence homology, signal transduction and pharmacology: The first group includes mGluR1 and mGluR5 which are coupled to $IP_3/Ca^{2+}$ signal transduction via activation of phospholipase C, whereas the members of group II, mGluR2 and mGluR3, as well as those of group III, mGluR4, mGluR6, mGluR7 and mGluR8, are negatively linked to adenylate cyclase. The conformationally restricted analogue of L-glutamic acid, (2S,2'R,3'R)-2-(2,3-dicarboxylcyclopropyl)-glycine (DCG-¼), has been found to be a particularly interesting compound, being a potent group II mGluR agonist, which is also active as an agonist at NMDA receptor site.

The synthesis of DCG-¼ described in the literature (Ohfune et al., International Patent Application WO 93-08158, Ohfune, et al., Bioorg. Med. Chem. Lett. 1993, 3, 15, and Ohfune et al., J. Med. Chem. 1996, 39, 407) is very long (more than 30 steps) and inefficient (only mg-quantities of the compound can be prepared). In addition, the synthesis of the radiolabeled compound is not possible using the described procedure.

SUMMARY OF THE INVENTION

In accordance with the present invention there is described the compound DCG-¼ as well as a short and efficient method for the synthesis of DCG-¼ in 8 steps starting from (−)-Feist's acid or in 3 steps starting from rac-trans-2,3-dicarbomethoxy-1-formyl-cyclopropane. The procedure described permits the synthesis of DCG¼ in g-quantities as well as the introduction of tritium in the position 1' of the molecule. DCG-¼ can be used as a pharmacological tool to study the function of group II mGluR (metabotropic glutamate receptor).

DETAILED DESCRIPTION OF THE INVENTION

The present invention is directed to a process for preparation of (2S,2'R,3'R)-2-(2,3-dicarboxycyclopropyl)-glycine and comprises the following steps:

a) brominating Feist's acid (1S,2S)-3-methylene-cyclopropane-1,2-dicarboxylic acid of formula

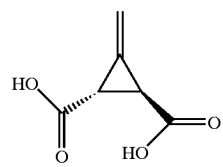

II to yield (1R,2R)-3-bromo-3-bromomethyl-cyclopropane-1,2-dicarboxylic acid of formula

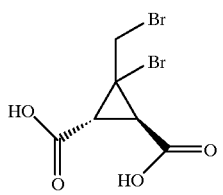

III b) forming the lactone (1RS,5R,6R)-1-bromo-4-oxo-bicyclo[3.1.0]hexane-6-carboxylic acid of formula IV on the structure of the compound of formula III

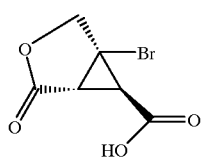

IV c) opening the lactone ring and esterifying the resultant compound to yield a compound of formula

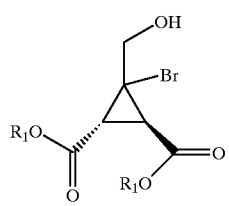

V wherein $R_1$ is lower alkyl, d) oxidizing the compound of formula V to yield (1R,2R)-3-bromo-1,2-dicarboalkyloxy-3-formyl-cyclopropane of formula

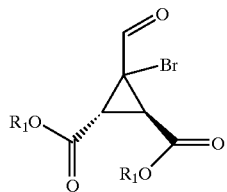

wherein $R_1$ is as described as above,
e) dehalogenating the compound of formula VI to yield (1R,2R)-1,2-dicarbomethoxy-3-formyl-cyclopropane of formula

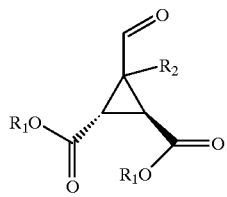

wherein $R_1$ is as described above and $R_2$ is hydrogen, and, optionally, introducing tritium in position 1' of the cyclopropyl ring to yield 3-[$^3$H]-(1R,2R)-1,2-dicarbomethoxy-3-formyl-cyclopropane of formula VII, wherein $R_2$ is tritium,
f) reacting the compound of formula VII or the compound (RS)-trans-2,3-dicarbomethoxy-1-formyl-cyclopropane with (R)-α-phenylglycinol and with a cyanide to yield (2S,2'R,3'R)-N-[(R)-2-hydroxy-1-phenyl-ethyl]-2-(2',3'-dicarbomethoxycyclopropyl)-glycinonitrile of formula

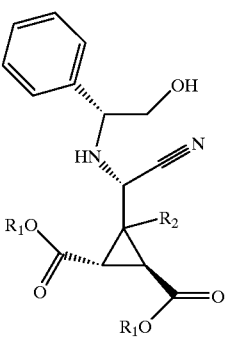

wherein $R_1$ and $R_2$ are as described above, and
g) cleaving off the directing group and hydrolyzing the ester- and nitrile groups to yield a compound of formula I.
The foregoing process steps are described in more detail as follows:
Procedure A
The synthesis of the enantiomerically pure compounds of formula VII in five steps starting from (−)-Feist's acid is described in this procedure.
Starting from (1R,2R)-3-bromo-1,2-dicarbomethoxy-3-formyl-cyclopropane (VI) it is possible to prepare (1R,2R)-1,2-dicarbomethoxy-3-formyl-cyclopropane (VII-1) as well as $^3$H-(1R,2R)-1,2-dicarbomethoxy-3-formyl-cyclopropane (VII-2).
Halogenation, preferentially bromination of (1S,2S)-3-methylene-cyclopropane-1,2-dicarboxylic acid (II) using standard methods yields (1R,2R)-3-bromo-3-bromomethyl-cyclopropane-1,2-dicarboxylic acid (III), which is then heated in water to yield (1RS,5R,6R)-1-bromo-4-oxa-bicyclo[3.1.0]hexane-6-carboxylic acid (IV). Opening of the lactone and esterification is performed with acids in alcohols, preferably sulfuric acid in MeOH, to yield (1R,2R)-3-bromo-1,2-dicarbomethoxy-3-hydroxymethyl-cyclopropane (V), which is then oxidized by use of standard methods, preferably PCC (pyridinium chlorochromate), to yield (1R,2R)-3-bromo-1,2-dicarbomethoxy-3-formyl-cyclopropane (VI). Compound II of (1S,2S)-3-methylene-cyclopropane-1,2-dicarboxylic acid is commercially available or it can be prepared according to methods known in the art, see for example [a) F. Feist, Chem. Ber. 1893, 26, 747; also commercially available. b) a modified procedure is described in: A. T. Blomquist, D. T. Longone, J. Am. Chem. Soc. 1959, 81, 2012. c) optical resolution: W. von E. Doering, H. D. Roth, Tetrahedron 1970, 26, 2825.]

Dehalogenation can be achieved by use of standard methods, preferably by treatment of (1R,2R)-3-bromo-1,2-dicarbomethoxy-3-formyl-cyclopropane (VI) with zinc in acetic acid or, alternatively, with tributyltin hydride in diethyl ether or other ethers to give (1R,2R)-1,2-dicarbomethoxy-3-formyl-cyclopropane (VII-1).

These methods, preferably the reaction with tributyl tin tritide can be used for the preparation of $^3$H-(1R,2R)-1,2-dicarbomethoxy-3-formyl-cyclopropane (VII-2).

Further reaction of (1R,2R)-1,2-dicarbomethoxy-3-formyl-cyclopropane (VII-1) and $^3$H-(1R,2R)-1,2-dicarbomethoxy-3-formyl-cyclopropane (VII-2) are performed according to procedure B to yield (2S,2'R,3'R)-2-(2,3-dicarboxylcyclopropyl)-glycine (I-1) [DCG-¼] and $^3$H-(2S,2'R,3'R)-2-(2,3-dicarboxylcyclopropyl)-glycine (I-2) [$^3$H-DCG-¼].
Procedure B This synthesis starts from (RS)-trans-2,3-dicarbomethoxy-1-formyl-cyclopropane (VII-3) which is prepared by the addition of dimethylsulfonium-3-carboxallylide to dimethyl fumarate and treatment of the formed cyclopropyl derivative with osmiumtetroxide/sodium metaperiodate according to a protocol described in the literature [Nordlander et al., J. Org. Chem. 39 (1974) 3814].

The key step of the synthesis is a diastereoselective Strecker-reaction involving the nucleophilic addition of a cyanide ion to the Schiffbase formed by condensation of the racemic aldehyde with optically active (α-aminoalcohols, preferentially (α-phenylglycinol. Reaction of the aldehyde with (R)-α-phenylglycinol in alcohols, preferentially methanol, at room temperature for 2 hours, followed by treatment of the Schiff' base with cyanide, preferentially trimethylsilyl cyanide, for 12 hours at room temperature yields a mixture of four α-amino nitrites as two major and two minor components in ca. 8:2 ratio.

Extensive column chromatography of the mixture followed by crystallization yields (2S,2'R,3'R)-N-[(R)-2-hydroxy-1-phenyl-ethyl]-2-(2',3'-dicarbomethoxycyclopropyl)glycinonitrile (VIII).

Cleavage of the directing groups can be performed by standard procedures, preferably oxidative cleavage with lead tetra acetate, acidic hydrolysis (6N HCl) and ion exchange chromatography on Dowex 50WX4 to afford (2S,2'R,3'R)-2-(2,3-dicarboxylcyclopropyl)-glycine (I) [DCG-¼].

The following reaction scheme illustrate the process steps for the preparation of the compound of formula I in more detail.

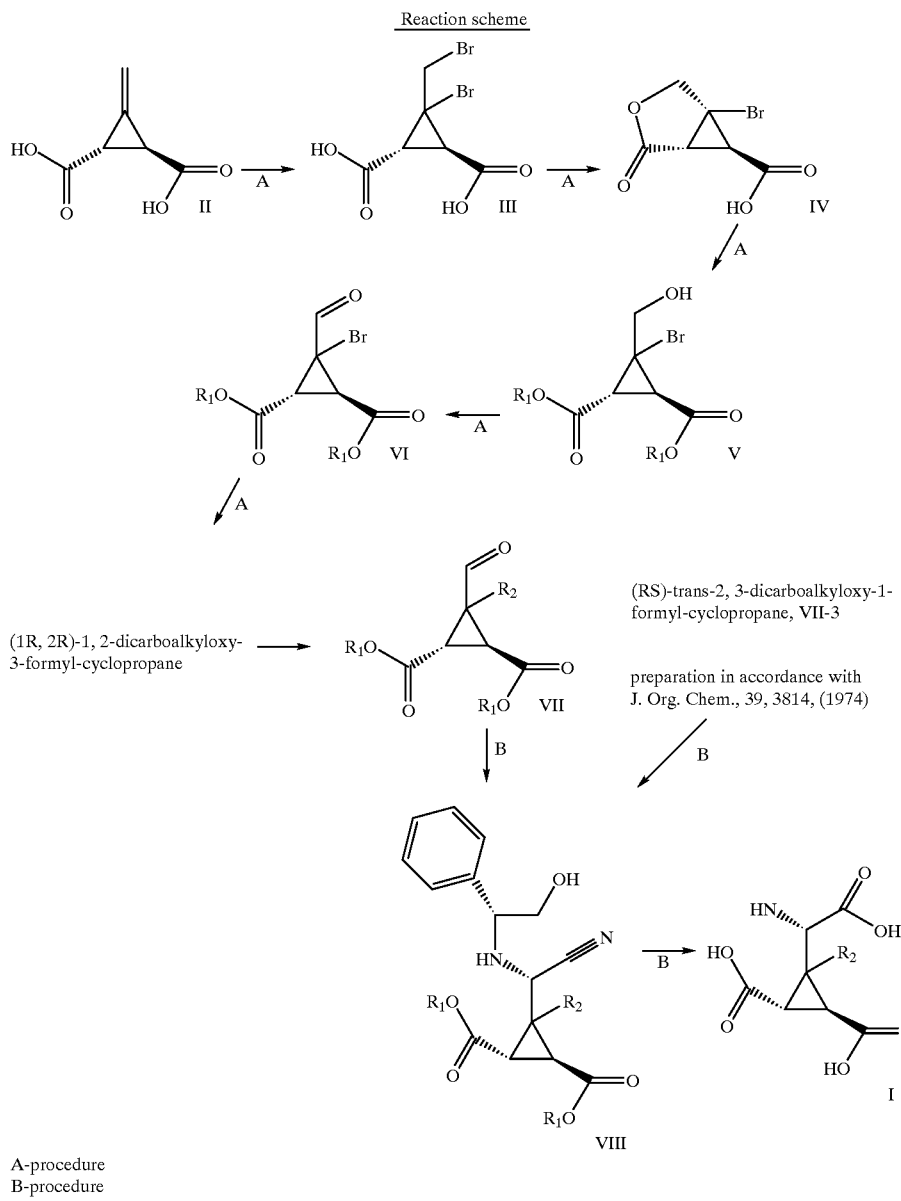

Exemplary embodiments of the present invention are set forth below. These examples are for purposes of exposition and are not to be construed as limiting.

Procedure A

Starting from (1S,2S)-3-methylene-cyclopropane-1,2-dicarboxylic acid [(−)-Feist's acid] (II)

a) (1R,2R)-3-bromo-3-bromomethyl-cyclopropane-1,2-dicarboxylic acid

To a cooled (0°) and stirred solution of (1S,2S)-3-methylene-cyclopropane-1,2-dicarboxylic acid [(−)-Feist's acid] (4.0 g, 28.2 mmol) in diethyl ether (250 ml) was added bromine (2 ml), and stirring continued over a period of 16 hours at room temperature. Filtration, evaporation of the solvent and crystallization of the crude product from dichloromethane/hexane yielded (1R,2R)-3-bromo-3-bromomethyl-cyclopropane-1,2-dicarboxylic acid (5.45 g, 64%) as a pale brown solid. mp 233° C. (dec.); $[\alpha]^{20}D=+80°$ (c=0.25 in MeOH); $^1$H NMR (DMSO-$d_6$): d 2.58 (d, J=6.5 Hz, 1H), 2.63 (d, J=6.5 Hz, 1H), 4.07 (d, J=11 Hz, 1H), 4.17 (d, J=11 Hz, 1H). MS (FAB) m/z 299, 301, 303 [M−H$^+$].

b) (1RS,5R,6R)-1-bromo-4-oxa-bicyclo[3.1.0]hexane-6-carboxylic acid

A solution of (1R,2R)-3-bromo-3-bromomethyl-cyclopropane-1,2-dicarboxylic acid (5.4 g, 17.9 mmol) in water (100 ml) was boiled under reflux conditions over a period of 4 hours. Filtration, evaporation of the solvent and column chromatography of the crude product (dichloromethane/methanol 9:1) gave 2.75 g of a solid. Further crystallization from dichloro-methane/hexane yielded (1RS,5R,6R)-1-bromo-4-oxa-bicyclo[3.1.0]hexane-6-carboxylic acid (2.41 g/61%) as a light yellow solid. mp 196–198° C.; $[\alpha]^{20}D=-36°$ (c=0.25 in MeOH); $^1$H NMR (DMSO-$d_6$): d 2.64 (d, J=3 Hz, 1H), 2.93 (d, J=3 Hz, 1H), 4.56 (d, J=10 Hz, 1H). 4.71 (d, J=10 Hz, 1H). MS (EI) m/z 220, 222 [M+], 202, 204 (48) [M+—H₂O], 123 (100) [M+—H₂O, —Br], 97 (98).

c) (1R,2R)-3-bromo-1,2-dicarbomethoxy-3-hydroxymethyl-cyclopropane

To a stirred solution of (1RS,5R,6R)-1-bromo-4-oxabicyclo[3.1.0]hexane-6-carboxylic acid (2.41 g, 10.9 mmol) in methanol (25 ml) was added sulfuric acid (conc., 2.5 ml) and stirring continued over a period of 2 hours. The reaction mixture was poured into ice/water (100 ml) and extracted with two 100 ml portions of ethyl acetate. The combined organic layers were washed with water (50 ml) and two 50 ml portions of saturated sodium hydrogen carbonate solution, dried (MgSO₄) and evaporated to yield (1R,2R)-3-bromo-1,2-dicarbomethoxy-3-hydroxymethyl-cyclopropane (2.85 g, 97%) as a light yellow oil. $[\alpha]^{20}D=+98.4°$ (c=0.25 in MeOH); ¹H NMR (CDCl₃): d 2.66 (dd, J=6, 8 Hz, 1H), 2.70 (d, J=6.5 Hz, 1H), 2.87 (d, J=6.5 Hz, 1H), 3.77 (s, 3H), 3.80 (s, 3H), 3.99 (dd, J=8, 12.5 Hz, 1H 4.16 (dd, J=6, 12.5 Hz, 1H). MS (EI) m/z 267, 269 [M+H+], 249, 251 (3) [M+—OH], 235, 237 (14) [M+—OMe], 207, 209 (94), 175, 177 (82), 169 (83), 155 (46), 113 (100), 59 (76).

d) (1R,2R)-3-Bromo-1,2-dicarbomethoxy-3-formyl-cyclopropane

To a stirred solution of (1R,2R)-3-bromo-1,2-dicarbomethoxy-3-hydroxymethyl-cyclopropane (2.8 g, 10.5 mmol) in dichloromethane (120 ml) was added pyridinium chlorochromate (3.35 g, 15.7 mmol) and stirring continued over a period of 16 hours. Diethyl ether (120 ml) was added to the reaction mixture, which was then filtered with the aid of a Whatman glass microfibre filter and evaporated. Column chromatography of the crude product (diethyl ether/hexane 1:1) yielded (1R,2R)-3-bromo-1,2-dicarbomethoxy-3-formyl-cyclopropane (1.93 g, 69%) as a white solid. mp 52° C.; $[\alpha]^{20}D=+108°$ (c=0.25 in MeOH): ¹H NMR (CDCl₃): d 3.16 (d, J=6.5 Hz, 1H), 3.27 (d, J=6.5 Hz, 1H), 3.76 (s, 3H), 3.83 (s. 3H), 9.26 (s, 1H). MS (EI) m/z 265, 267 [M+H+], 233, 235 (24) [M+—OMe], 204, 206 (24), 176, 178 (44), 153 (100), 125 (95), 59 (69).

e) (1R,2R)-1,2-dicarbomethoxy-3-formyl-cyclopropane

A mixture of (1R,2R)-3-bromo-1,2-dicarbomethoxy-3-formyl-cyclopropane (428 mg, 1.6 mmmol), zinc powder (230 mg, 3.5 mmol) and acetic acid (2 ml) was stirred at room temperature over a period of 4 hours. Filtration, evaporation and column chromatography yielded (1R,2R)-1,2-dicarbomethoxy-3-formyl-cyclopropane (265 mg, 88%) as a colourless oil. $[\alpha]^{20}D=-48°$ (c=1 in MeOH); ¹H NMR (CDCl₃): d 2.53 (ddd, J=5, 6, 8 Hz, 1H), 2.71 (dd, J=6, 8 Hz, 1H), 3.01 (t, J=6 Hz, 1H), 3.76 (s, 6H), 9.42 (d, J=5 Hz, 1H); MS (FAB) m/e 187 [M+H+].

f) (2S,2'R,3'R)-N-[(R)-2-hydroxy-1-phenyl-ethyl]-2-(2',3'-dicarbomethoxy-cyclopropyl)-glycinonitrile To a solution of (1R,2R)-1,2-dicarbomethoxy-3-formyl-cyclopropane (256 mg, 1.38 mmol) in methanol (15 ml) was added (R)-a-phenylglycinol (189 mg, 1.38 mmol), and the resulting solution stirred at room temperature for 5 hours. After cooling to 0° C., TMSCN (0.34 ml, 2.75 mmol) was added, and the resulting mixture was stirred for 16 hours at room temperature. Evaporation of the solvent gave a yellow oil, which was then purified by column chromatography (ethyl acetate/hexane 1:1) to yield (2S,2'R,3'R)-N-[(R)-2-hydroxy-1 -phenyl-ethyl]-2-(2',3'-dicarbomethoxy-cyclopropyl)-glycinonitrile (387 mg, 84%) as a colourless oil.

Procedure B

Starting from (RS)-trans-2,3-dicarbomethoxy-1-formyl-cyclopropane (VII-3)

a) (2S,2'R,3'R)-N-[(R)-2-hydroxy-1-phenyl-ethyl]-2-(2',3'-dicarbo-methoxycyclopropyl)-glycinonitrile To a solution of (RS)-trans-2,3-dicarbomethoxy-1-formyl-cyclopropane (3.11 g, 16.7 mmol) in methanol (110 ml) was added (R)-α-phenylglycinol (2.29 g, 16.7 mmol), and the resulting solution stirred at room temperature for 2 hours. After cooling to 0° C., TMSCN (4.2 ml, 33.4 mmol) was added, and the resulting mixture stirred for 16 hours at room temperature. Evaporation of the solvent gave a yellow oil, which was then purified as follows:

(1) column chromatography (ethyl acetate/hexane 2:1) yielded 1.32 g (24%) of a colorless oil, 2.15 g (39%) of a light yellow oil (mixture) and 1.51 g (27%) of a colorless oil. (2) column chromatography (ethyl acetate/hexane 2:1) of the mixture (2.15 g) gave 0.98 g of a colorless oil and 1.08 g of a colorless oil. Further separation of the mixtures was performed by crystallization from diethylether/hexane to yield (2S,2'R,3'R)-N-[(R)-2-hydroxy-1-phenyl-ethyl]-2-(2',3'-dicarbo-methoxycyclopropyl)-glycinonitrile (1.43 g, 26%) as a light yellow oil. IR (KBr) v 1070 (OH), 1190 (ester), 1720 (ester), 2227 (CN). MS (FAB) m/z 333 (M+H+). $[\alpha]^{20}D=-90.4°$ (c=0.25 in MeOH). NMR (CDCl₃): d 1.61 (br, 1H), 1.89 (br, 1H), 2.19 (m, 2H), 2.42 (dd, J=8.5, 9 Hz, 1H), 3.61 (m, 1H), 3.64 (s, 3H), 3.74 (m, 1H), 3.75 (s,3H), 3.80 (dd, J=4, 9 Hz, 1H), 4.09 (dd, J=4, 8 Hz, 1H), 7.36 (m, 5H).

b) (2S,2'R,3'R)-2-(2,3-dicarboxylcyclopropyl)-glycine (DCG-¼)

Lead(IV) acetate (2.10 g, 4.73 mmol) was added to a cold (0° C.), stirred solution of (2S,2'R,3'R)-N-[(R)-2-hydroxy-1-phenyl-ethyl]-2-(2',3'-dicarbo-methoxy-cyclopropyl)-glycinonitrile (1.43 g, 4.30 mmol) in anhydrous methanol-dichloromethane (36 ml, 1:1). After 15 min, water-(36 ml) was added and the resulting mixture was filtered with the aid of Celite. After evaporation of the solvent, the residue was refluxed in 6 N HCl (100 ml) for 12 hours. The reaction mixture was washed twice with dichloromethane (30 ml each) and evaporated to dryness. The residue was submitted to ion exchange resin chromatography (Dowex 50WX4) to yield (2S,2'R,3'R)-2-(2,3-dicarboxylcyclopropyl)-glycine (0.55 g, 54%) as a white, hygroscopic foam (diammonium salt). mp 171–173° C. (dec.). $[\alpha]^{20} D=-43.6°$ (c=0.25 in H₂O). NMR (D₂O): d 1.93 (ddd, J=6, 9.5, 10 Hz, 1H), 2.07 (dd, J=5.5, 6 Hz), 2.17 (dd, J=5.5, 9.5 Hz), 4.03 (d, J=10 Hz). MS (FAB) m/z 204 (M+H+).

Synthesis of ³H-(2S,2'R,3'R)-2-(2,3-dicarboxylcyclopropyl)-glycine (³H-DCG-¼) (I-2) starting from (1R,2R)-3-bromo-1,2-dicarbomethoxy-3-formyl-cyclopropane (VI).

a) ³H-(1R,2R)-1,2-dicarbomethoxy-3-formyl-cyclopropane

Starting with 250 μl of 1.39 M n-butyl lithium (0.347 mmoles) a solution of 0.78 ml of lithium triethylborane tritide was prepared according to the method of Andres et al. [H. Andres et al., PCT Int. Appl. WO 91 15,858]:

0.94 ml of tri-n-butyltinchloride was added and the solution stirred for 15 min. The reaction mixture was lyophilized, the vacuum was relieved with dry nitrogen and the two-necked flask was removed from the tritiation apparatus. The residue was suspended in 2 ml of n-heptane and the suspension was applied onto a 0.5 g silicagel cartridge (Chromabond, Machery Nagel, #730073). The cartridge was rinsed with three 1 ml-aliquots of n-heptane. The total $^3$H-activity of the n-heptane eluate was 5.03 Ci. The eluate was lyophilized and the residue of pure tri-n-butyltintritide was dissolved in 1 ml of cyclohexane-tetrahydrofuran 1:1 under argon. 48 mg (0.181 mmoles of (1R,2R)-3-bromo-1, 2-dicarbomethoxy-3-formylcyclopropane and 1.2 mg of 2,2'-azobisisobutyronitrile (AIBN) was added and the reaction mixture stirred for 18 h at 50° C. Then 1 ml of saturated potassium fluoride solution was added and stirring was continued for 1 hour at room temperature. Partitioning between diethylether and ice/water, washing the organic layers with saturated sodium chloride solution and drying over anhydrous sodium sulfate yielded a crude product with total $^3$H-activity of 4.84 Ci. Column chromatography on 9 g LichroprepSi60 15–25 μm (Merch #1.09336) with n-hexane-diethylether 1:1 afforded 2.18 Ci$^2$) of product. The radiochemical purity was 96% according to TLC. The loss of $^3$H-acitivity during chromatography was probably due to hydrogen exchange catalyzed by the slightly acidic silica gel. It is therefore recommended to omit chromatography at this stage of the synthesis.

b) $^3$H-(2S,2'R,3'R)-N-[(R)-2-hydroxy-1-phenyl-ethyl]-2-(2', 3'-dicarbomethoxy-cyclopropyl)-glycinonitrile 1.3 Ci of 3-[$^3$H]-(1R,2R)-1,2-dicarbomethoxy-3-formyl-cyclopropane and 6.8 mg (0.05 mmoles) of D-phenylglycinol in 0.45 ml dry methanol was stirred for 6 hours at room temperature 12 μl (0.096 mmoles) of trimethylsilylcyanide was added at 0° C. and stirring was continued for 15 hours at room temperature. Column chromatography on 7 g LichroprepSi60 15.25 μm with n-hexane-ethyl acetate 1:1 afforded 456 mCi $^3$H-activity of product (2S,2'R,3'R)-N-[(R)-2-hydroxy-1-phenyl-ethyl]-2-(1'-[$^3$H], 2,3'-dicarbomethoxy-cyclopropyl)-glycinonitrile.

c) $^3$H-(2S,2'R,3'R)-2-(2,3-dicarboxylcyclopropyl)-glycine (DCG-¼)

To a solution of 4.2 mg (0.0126 mmoles) of 1 (total $^3$H-activity 220 mCi) in 0.5 ml of dichloromethane-methanol 1:1 was added 6.7 mg (0.015 mmoles) lead tetraacetate at 0° C. under argon and the mixture stirred for 15 min. at this temperature. The solvents were evaporated, 1.5 ml of 6N hydrochloric acid was added and the reaction mixture stirred at 100° C. for 15 hours. The crude product was partitioned between dichloromethane and water and the aqueous phase was lyophilized. The residue was dissolved in 5 ml of water and this solution applied onto a small cation exchange column (5×50 mm, 0.6 g Dowex 50W×4H+- form). After rinsing with 15 ml of water the DCG-¼ was eluted with 20 ml of 2N ammonium hydroxide solution. HPLC-purification of 35 mCi of this sample afforded 14.2 mCi of product. HPLC-conditions: column: LiChrocart Superspher RP-18e 5 μm 4×250 mm Merck #16858 mobile phase: 20 mM orthophosphoric acid, flow rate: 0.5 ml/min, UV-detection at 205 nm. To get rid of the orthophosphoric acid, the solution of $^3$H-DCG-¼ was applied onto a SP-Sephadex cation exchange column (H+-form, 10×100 mm). After washing with two 10 ml aliquots of water, the $^3$H-DCG-¼ was eluted with 2N ammonium hydroxide solution using a fraction collector. Total $^3$H-activity of product 11.7 mCi. The radiochemical purity was 98.3% according to TLC (silica gel 60, n-butanol-acetic acid-water 3:1:1). The specific activity determined HPLC was 17.5 Ci/mmole.

We claim:

1. A process for the preparation of (2S,2'R,3'R)-2-(2,3-dicarboxyl-cyclopropyl)-glycine or (2S,2'R,3'R)-2-(1'-[$^3$H], 2',3'-dicarboxyl-cyclopropyl)-glycine of the formula

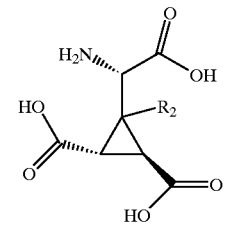

I wherein R$_2$ is hydrogen or tritium, which comprises the steps of a) brominating Feist's acid (1S,2S)-3-methylene-cyclopropane-1,2-dicarboxylic acid of formula

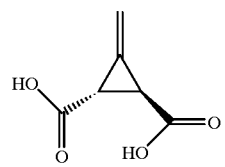

II to yield (1R,2R)-3-bromo-3-bromomethyl-cyclopropane-1, 2-dicarboxylic acid of formula

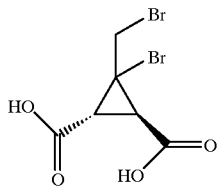

III b) forming the lactone (1RS,5R,6R)-1-bromo-4-oxo-bicyclo [3.1.0]hexane-6-carboxylic acid of formula IV on the structure of the compound of formula III

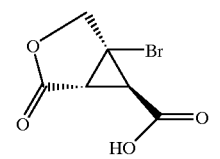

IV c) opening the lactone ring and esterifying the resultant compound to give a compound of formula

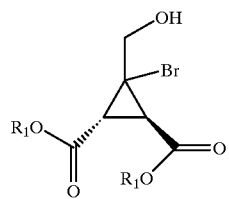

wherein $R_1$ is lower alkyl, d) oxidizing the compound of formula V to yield (1R,2R)-3-bromo-1,2-dicarboalkyloxy-3-formyl-cyclopropane of formula

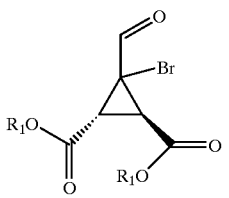

wherein $R_1$ is lower alkyl, e) dehalogenating the compound of formula VI to yield (1R,2R)-1,2-dicarbomethoxy-3-formyl-cyclopropane of formula

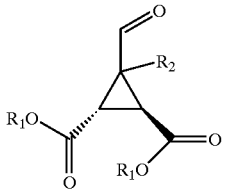

wherein $R_1$ is lower alkyl and $R_2$ is hydrogen, and, if desired, introducing tritium in position 1' of the cyclopropyl ring to yield 3-[$^3$H]-(1R,2R)-1,2-dicarbomethoxy-3-formyl-cyclopropane of formula VII, wherein $R_2$ is tritium, f) reacting the compound of formula VII or the compound (RS)-trans-2,3-dicarbomethoxy-1-formyl-cyclopropane with (R)-α-phenylglycinol and a cyanide to yield (2S,2'R,3'R)-N-[(R)-2-hydroxy-1-phenyl-ethyl]-2-(2',3'-dicarbomethoxycyclopropyl)-glycinonitrile of formula

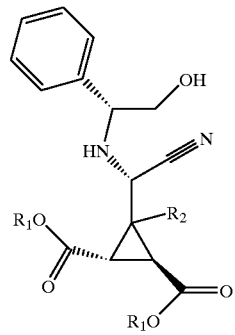

wherein $R_1$ is lower alkyl and $R_2$ is hydrogen or tritium, and g) cleaving off the directing group and hydrolyzing the ester- and nitrile groups to yield the compound of formula I.

2. A process in accordance with claim 1, wherein the bromination of step (b) is carried out in diethyl ether at room temperature.

3. A process in accordance with claim 1, wherein the lactone ring of step (b) is prepared in boiled water under reflux conditions.

4. A process in accordance with claim 1, wherein the process of step (c) is effected with acid in alcohol.

5. A process in accordance with claim 4, wherein the acid is sulfuric acid and the alcohol is methanol or ethanol.

6. A process in accordance with claim 1, wherein the oxidation of step (d) is carried out with pyridinium chloro chromate (PCC).

7. A process in accordance with claim 1, wherein the dehalogenation of step (e) is carried out with zinc in acetic acid or with tributyl tin-hydride in diethylether.

8. A process in accordance with claim 7, wherein tritium is introduced by addition of lithium triethylborane tritide.

9. A process in accordance with claim 1, wherein the reaction of step (f) is carried out in methanol at room temperature.

10. A process in accordance with claim 9, wherein the cyanide is trimethylsilyl cyanide.

11. A process in accordance with claim 9, wherein four α-amino-nitrile compounds of formula VIII are obtained.

12. A process in accordance with claim 1, wherein the directing group of step (g) may be cleaved off by oxidative cleavage, acidic hydrolysis or ion exchange chromatography.

13. A process for the preparation of (2S,2'R,3'R)-2-(2,3-dicarboxyl-cyclopropyl)-glycine or (2S,2'R,3'R)-2-(1'-[$^3$H],2',3'-dicarboxyl-cyclopropyl)-glycine of the formula

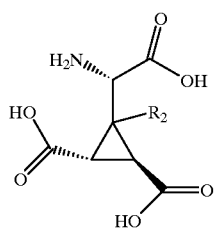

wherein R₂ is hydrogen or tritium, which process comprises a) dehalogenating a compound of formula

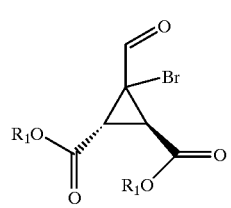

to yield (1R,2R)-1,2-dicarbomethoxy-3-formyl-cyclopropane of formula

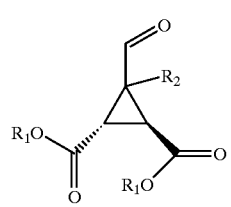

wherein $R_1$ is lower alkyl and $R_2$ is hydrogen, and if desired, introducing tritium in position 1 of the cyclopropyl ring to give 3-[³H]-(1R,2R)-1,2-dicarbomethoxy-3-formyl-cyclopropane of formula VII, wherein $R_2$ is tritium, and b) reacting a compound of formula VII or the compound (RS)-trans-2,3-dicarbomethoxy-1-formyl-cyclopropane with (R)-α-phenylglycinol and with a cyanide to give (2S, 2'R,3'R)-N-[(R)-2-hydroxy-1-phenyl-ethyl]-2-(2',3'-dicarbomethoxycyclopropyl)-glycinonitrile of formula

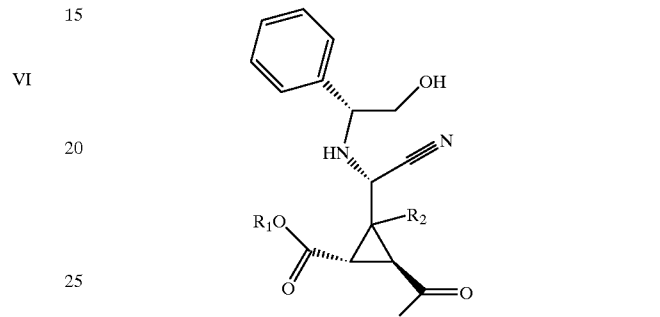

wherein $R_1$ is lower alkyl and $R_2$ is hydrogen or tritium, and c) cleaving off the directing group and hydrolyzing the ester- and nitrile groups to give a compound of formula I.

\* \* \* \* \*